United States Patent [19]

Suzuki

[11] 4,156,686

[45] May 29, 1979

[54] CATALYTIC REACTION OF ALKENYL SUCCINIC ANHYDRIDES AND OLEFINS

[75] Inventor: Shigeto Suzuki, San Francisco, Calif.

[73] Assignee: Chevron Research Company, San Francisco, Calif.

[21] Appl. No.: 613,597

[22] Filed: Sep. 15, 1975

[51] Int. Cl.$^2$ ............................................. C07D 307/60
[52] U.S. Cl. .................................................. 260/346.74
[58] Field of Search .................. 260/346.8, 346.3, 326, 260/346.8 R, 346.75

[56] References Cited

U.S. PATENT DOCUMENTS 2,764,597  9/1956  Barney .............................. 260/346.3

OTHER PUBLICATIONS

Weygand/Hilgetag, *Preparative Organic Chemistry*, 1972, John Wiley & Sons, New York, pp. 1054–1056.

*Primary Examiner*—Alan L. Rotman
*Assistant Examiner*—Bernard Dentz
*Attorney, Agent, or Firm*—D. A. Newell; John Stoner, Jr.; A. T. Bertolli

[57] ABSTRACT

A process for preparing alkyl maleic anhydrides which comprises heating a lower alkenyl succinic anhydride in the presence of a catalytic amount of ruthenium or a catalytic salt thereof under conditions effective to isomerize the alkenyl succinic anhydride.

4 Claims, No Drawings

CATALYTIC REACTION OF ALKENYL SUCCINIC ANHYDRIDES AND OLEFINS

BACKGROUND OF THE INVENTION

This invention relates to the preparation of select alkyl maleic anhydrides from alkenyl succinic anhydrides. Alkyl maleic anhydrides prepared in accordance with this invention are useful intermediates in the preparation of alpha-alkyl-beta-alkenyl succinic anhydrides which are useful paper sizing agents and gasoline detergent additives.

A variety of processes for the preparation of alkenyl succinic anhydrides have been known and used for many years. For instance, U.S. Pat. No. 2,411,215, granted Nov. 16, 1946, and U.S. Pat. No. 3,819,660, granted June 25, 1974, describe the 1,2- addition reaction of monoolefins with maleic anhydride to prepare the corresponding alkenyl succinic anhydride. In general, the reaction proceeds according to the reaction scheme:

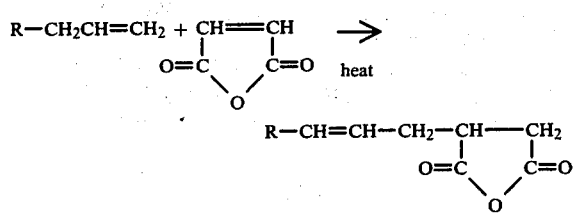

While alkenyl succinic anhydrides are useful products, there is a continuing need to develop a simple process for preparing alkyl maleic anhydrides. Toward this aim, it would be desirable to develop a means of isomerizing the alkenyl exocyclic double bond of alkenyl succinic anhydrides back into the anhydride ring to form alkyl maleic anhydrides.

The use of various acid catalysts to isomerize aliphatic alkenes is described in the prior art. For instance, Noller (Ed.), "Chemistry of Organic Compounds 3rd", W. B. Saunders (1966) describes the acid-catalyzed interconversion of 1-butene and cis- and trans-2-butene. Additionally, Noller discloses the thermally induced rearrangement of itaconic anhydride to citraconic anhydride.

SUMMARY OF THE INVENTION

The process of the present invention comprises heating a lower alkenyl succinic anhydride of the formula

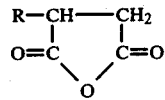

wherein R is an alkenyl group containing from about 3 to 7 carbon atoms, at a temperature below about 250° C. in the presence of a catalytic amount of ruthenium or a catalytic salt thereof.

DETAILED DESCRIPTION OF THE INVENTION

The present invention relates to the discovery that select alkyl maleic anhydrides can be prepared from corresponding alkenyl succinic anhydrides utilizing a catalyst comprising from about 0.1% to 15.0%, by weight, or ruthenium or its catalytic salts.

The alkenyl succinic anhydrides suitable for use in the practice of this process can be obtained by a variety of well-known reactions. In general, alkenyl succinic anhydrides are prepared by thermal condensation of maleic anhydrides with monoolefins. U.S. Pat. Nos. 2,411,215 and 3,819,660, previously mentioned, describe typical preparations.

More particularly, alkenyl succinic anhydrides suitable for use herein are characterized by an alkenyl substituent containing from about 3 to 7, preferably from about 3 to 5, carbon atoms. It has been found that the higher-chain-length alkenyl succinic anhydrides, containing greater than about 7 carbon atoms in the alkenyl group, when heated in the presence of a ruthenium catalyst, predominantly yield the alkenyl succinic anhydride isomers and only minor amounts of the desired maleic anhydride isomer. Accordingly, alkenyl succinic anhydrides having greater than about 7 carbon atoms in the alkenyl substituent are unsatisfactory for use herein.

Illustrative suitable alkenyl succinic anhydrides include, for example, allyl succinic anhydride, butenyl succinic anhydride, hexenyl succinic anhydride, heptenyl succinic anhydride, 4,4-dimethyl pentenyl succinic anhydride, 3,4-dimethyl pentenyl succinic anhydride, and the like. The position of the alkenyl double bond is not critical to the isomerization; however, alkenyl groups having the double bond in the 1,2 or 2,3 position are preferred. It has been found that as the exocyclic double bond is positioned farther than the 2,3 position from the anhydride ring the process will produce a mixture of products in which the double bond is predominantly in the exocyclic positions. Accordingly, alkenyl succinic anhydrides having the alkenyl double bond adjacent, or nearly adjacent to, the anhydride ring are preferred. Illustrative preferred alkenyl succinic anhydrides include, for example, allyl succinic anhydride and but-2-enyl succinic anhydride.

It has been found that only select Group VIII noble transition metals will efficiently catalyze the desired isomerization. The present process relates to the isomerization of alkenyl succinic anhydrides in the presence of catalytic amounts of ruthenium or a catalytic salt thereof.

The amount of catalyst present in the system can vary over a wide range. For example, amounts ranging from about 0.1% to about 15.0%, by weight of alkenyl succinic anhydride, are satisfactory, and amounts ranging from about 1.0% to about 5.0% are preferred.

The ruthenium catalysts suitable for use in the isomerization of alkenyl succinic anhydrides include both nonhomogenous catalysts, for example ruthenium on a solid support such as carbon, and homogenous soluble catalysts such as the soluble organic and inorganic ruthenium salts.

Suitable soluble homogenous ruthenium catalysts include, for example, organic and inorganic salts of the formula

wherein L is nonionic organic ligand complexed to the ruthenium; X is an inorganic anionic ligand bound to the ruthenium; n is 0 to 5; m is 0 to 3; and m+n is 3 to 6. It is understood, of course, that m+n represents the coordination number of ruthenium, i.e., three-, four-, five- or six-coordinate, and that m represents the valence or oxidation state of the ruthenium moiety. Additionally, the ruthenium compound depicted represents only the empirical composition which may exist in a dimeric or polymeric form.

In accordance with the above formula, suitable non-ionic ligands complexed to the ruthenium, L, include, for example, water, carbon monoxide, olefins, organophosphines, organoarsines, organostibines, and organobismuthines. Suitable anionic ligands bound to ruthenium, X, include, for example, halides such as chloride, bromide and iodide; nitrite; and hydride.

Preferred L ligands include carbon monoxide and hydrocarbyl phosphines such as triphenylphosphines and trialkylphosphines. Preferred X ligands include halides such as chloride, bromide, and iodide.

Illustrative ruthenium catalysts suitable for use herein include ruthenium; ruthenium halides such as $RuCl_3$, $RuCl_3.3H_2O$, $RuBr_3$ and $RuI_3$; ruthenium carbonyl halides such as $RuI_2(CO)_2$, $Ru(CO)_3Cl_2$, and $Ru(CO)_2I_3$; ruthenium carbonyls such as $Ru(CO)_5$ and $[Ru(CO)_4]_3$, ruthenium organophosphines such as $Ru(CO)_2]P(CH_3)_3]_3$, $Ru(CO)_3[P(C_6H_5)_3]_2$, $RuCl_2(CO)[P(C_6H_5)_3]_3$, $RuHCl(CO)P(C_6H_5)_3$; and ruthenium compounds such as $RuCl_2(CO)[As(C_6H_5)_3]_3$ and $Ru(CO)_2[Sb(C_6H_5)_3]_3$.

Preferred catalysts include ruthenium and ruthenium diacetylacetonate.

The isomerization process of the invention is conducted in a fluid phase, i.e., either gaseous or liquid phase, in the presence or in the absence of an inert diluent. The process is carried out by intimately contacting the alkenyl succinic anhydride with the ruthenium catalyst. Although isomerization will proceed at moderate temperatures and pressures, for most practical applications reaction temperatures ranging from about 80° C. to 250° C. are satisfactory, and temperatures of from about 150° C. to about 230° C. are preferred. Within this temperature range, reaction time will vary from a few minutes to a few hours. The process is conducted at or above atmospheric pressure; pressures from about 1 atmosphere to 200 atmospheres are satisfactory.

At the conclusion of isomerization, equilibrium is reached between the various exocyclic alkenyl succinic anhydrides and alkyl maleic anhydride. Alkyl maleic anhydride can be recovered by conventional means, such as distillation, and the alkenyl succinic anhydrides can be recycled for further isomerization.

A principal advantage of the present process resides in the relatively high yield of alkyl maleic anhydride isomer obtained at equilibrium. While yields will vary depending upon such factors as the choice of starting material, catalyst and temperature of reaction) it has been found that yields on the order of at least 40%, by weight, of alkyl maleic anhydride are typical.

Another advantage of the present process for preparing alkyl maleic anhydrides is that a second olefinic moiety may be added to the unsubstituted ring carbon atom, thereby providing a simple synthetic route to alpha-alkyl-beta-alkenyl succinic anhydrides, useful as detergent compounds. The overall reaction process typically proceeds according to the scheme:

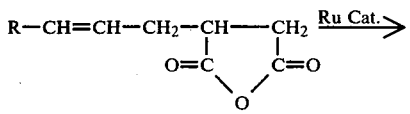

(1)

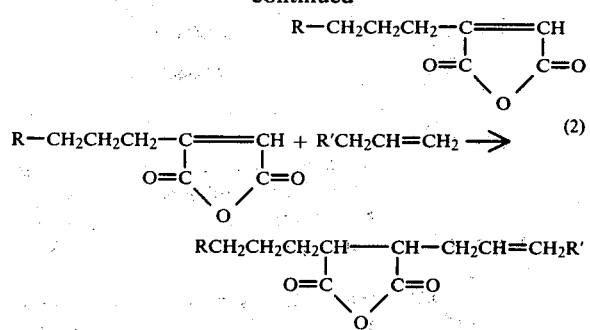

(2)

Although schematically presented as a two-step reaction, in practice alpha-alkyl-beta-alkenyl succinic anhydrides can be prepared, in accordance with this invention, by heating a mixture comprising an alkenyl succinic anhydride and an olefin in the presence of a catalytic amount of ruthenium, as described above. This process is believed to kinetically favor the isomerization to the intermediate maleic anhydride, thereby providing high yields of desired product.

In the above process, the second olefin molecule may be of any chain length; however, in many applications olefins containing an average of at least 8 carbon atoms are preferred.

EXAMPLES

The following examples illustrate the practice of this invention, but are not intended to be limiting thereof.

Example I—Isomerization of allyl succinic anhydride—60 minutes 2.0 g of allyl succinic anhydride were placed in a sealed reaction vessel. 0.05 g of ruthenium (5%) on a carbon support (2.5%, by weight based on anhydride) were added. The reaction mixture was heated to a temperature of 200° C. and reaction was allowed to proceed for approximately 60 minutes.

After 60 minutes, the reaction product was allowed to cool to room temperature, and gas chromatographic analysis of the product confirmed a product distribution of 34.7% propyl maleic anhydride and the balance propenyl succinic anhydride.

An equivalent amount of butenyl succinic anhydride, hexenyl succinic anhydride, heptenyl succinic anhydride, 4,4-dimethyl pentenyl succinic anhydride and 3,4-dimethyl propenyl succinic anhydride, respectively, is substituted for allyl succinic anhydride and isomerized in a like fashion.

An equivalent amount of ruthenium trichloride, ruthenium diacetylacetonate, and ruthenium carbonyl dibromide, respectively, is substituted for ruthenium on a carbon support and substantially equivalent results are achieved.

Example II—Isomerization of allyl succinic anhydride—120 minutes

Following the procedure of Example I, 2.0 g of allyl succinic anhydride were heated in the presence of 0.05 g of ruthenium (5%) on a carbon support (2.5% by weight) to a temperature of 200° C.

After 120 minutes, the reaction product was allowed to cool to room temperature, and gas chromatographic analysis of the product confirmed a product distribution of 44.9% propyl maleic anhydride and the balance propenyl succinic anhydride.

An equivalent amount of butenyl succinic anhydride, hexenyl succinic anhydride, heptenyl succinic anhydride, 4,4-dimethyl pentenyl succinic anhydride and 3,4-dimethyl propenyl succinic anhydride, respectively, is substituted for allyl succinic anhydride and isomerized in a like fashion.

An equivalent amount of ruthenium trichloride, ruthenium diacetylacetonate, and ruthenium carbonyl dibromide, respectively, is substituted for ruthenium on a carbon support and substantially equivalent results are achieved.

Example III—Isomerization of allyl succinic anhydride—180 minutes

Following the procedure of Example I, 3.0 g of allyl succinic anhydride was heated in the presence of 0.05 g of rutheniumdiacetylacetonate at 200° C. Aliquots were removed hourly for analysis. The product distribution remained essentially unchanged after 3 hours. Analysis at 3 hours showed the reaction mixture to contain 52.4% propylmaleic anhydride, the remainder being propenyl succinic anhydrides.

Example IV—Preparation of alpha-alkyl-beta-alkenyl succinic anhydrides 1.30 g of allyl succinic anhydride. 2.25 g of 1-octene and 0.025 g of hydroquinone were placed in a sealed reaction vessel. 0.039 g of ruthenium (5%) on a carbon support were added. The reaction mixture was heated to a temperature of 230° C. and allowed to proceed for 24 hours. The reaction product was analysed by gas chromatography which showed that 72% of the initially added allyl succinic anhydride was converted mainly to alpha-propyl-beta-octenyl succinic anhydride.

What is claimed is:

1. A process for preparing alpha-alkyl-beta-alkenyl succinic anhydrides which comprises heating a mixture comprising an alkenyl succinic anhydride of the formula

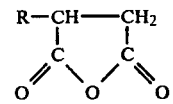

wherein R is alkenyl containing 3 to 7 carbon atoms and an olefin at a temperature below about 250° C. in the presence of a catalytic amount of ruthenium or a catalytic salt of the formula

wherein L is water or a nonionic organic ligand selected from the group consisting of carbon monoxide, olefins, organophosphines, organoarsines, organostibines, and organobismuthines complexed to the ruthenium; X is an inorganic anionic ligand selected from the group consisting of halides, nitrite, and hydride bound to the ruthenium; n is 0 to 5; m is 0 to 3; and m+n is 3 to 6.

2. A process according to claim 1 wherein said alkenyl succinic anhydride is allyl succinic anhydride.

3. A process according to claim 1 wherein the catalyst is selected from the group consisting of ruthenium and ruthenium diacetylacetonate.

4. A process according to claim 1 wherein said temperature is in the range of from about 80° C. to about 250° C.